US012576068B2

(12) United States Patent
Roessle et al.

(10) Patent No.: US 12,576,068 B2
(45) Date of Patent: Mar. 17, 2026

(54) COMPOSITIONS CONTAINING AMINO ACIDS AND METHODS OF USING SUCH COMPOSITIONS FOR TREATING SARCOPENIA

(71) Applicant: SOCIETE DES PRODUITS NESTLE S.A., Vevey (CH)

(72) Inventors: Claudia Roessle, Morges (CH); Denis Breuille, Lausanne (CH); Eugenia Migliavacca, Lausanne (CH); Jerome Feige, Crissier (CH)

(73) Assignee: Societe des Produits Nestle S.A., Vevey (CH)

( * ) Notice: Subject to any disclaimer, the term of this patent is extended or adjusted under 35 U.S.C. 154(b) by 723 days.

(21) Appl. No.: 17/907,451

(22) PCT Filed: Apr. 1, 2021

(86) PCT No.: PCT/EP2021/058555
§ 371 (c)(1),
(2) Date: Sep. 27, 2022

(87) PCT Pub. No.: WO2021/198400
PCT Pub. Date: Oct. 7, 2021

(65) Prior Publication Data
US 2023/0131476 A1      Apr. 27, 2023

Related U.S. Application Data

(60) Provisional application No. 63/003,495, filed on Apr. 1, 2020.

(51) Int. Cl.
*A61K 31/4172* (2006.01)
*A61K 31/198* (2006.01)
(Continued)

(52) U.S. Cl.
CPC ........ *A61K 31/4172* (2013.01); *A61K 31/198* (2013.01); *A61K 31/405* (2013.01); *A61K 31/675* (2013.01); *A61P 21/00* (2018.01)

(58) Field of Classification Search
CPC .............. A61K 2300/00; A61K 31/194; A61K 31/198; A61K 31/405; A61K 31/4172;
(Continued)

(56) References Cited

U.S. PATENT DOCUMENTS

2009/0181903 A1 * 7/2009 Wolfe ................... A61K 31/70
514/23
2020/0230093 A1 * 7/2020 Giorgetti ................. A61P 25/28

FOREIGN PATENT DOCUMENTS

CN      103974631 A      8/2014
CN      105120689 A      12/2015
(Continued)

OTHER PUBLICATIONS

Suidasari et al. "Dietary vitamin B6 modulates the gene expression of myokines, Nrf2-related factors, myogenin and HSP60 in the skeletal muscle of rats" Experimental and Therapeutic Medicine, 2017, vol. 14, pp. 3239-3246.
(Continued)

*Primary Examiner* — Savitha M Rao
(74) *Attorney, Agent, or Firm* — K&L Gates LLP

(57) ABSTRACT

A composition contains one or more aromatic amino acids and optionally vitamin B6. The composition may be an oral nutritional composition, for example a nutritional supplement, an oral nutritional supplement, a food product, a food for special medical purpose (FSMP). The composition can be in a form of a powder, a powdered stick, a capsule or a solution. The composition can be administered to an individual in need thereof orally or intravenously for preventing and/or treating sarcopenia, a loss of and/or improving skel-
(Continued)

Model with interaction

- - - high func B6, one sd above the mean
—— mean func B6
······ low func B6, one sd below the mean D3Cr muscle mass/ht^2, kg/m^2 serum concentration of Aromatic AA, scaled etal muscle mass, lean muscle mass, skeletal muscle strength and/or skeletal muscle function.

12 Claims, 7 Drawing Sheets

(51) Int. Cl.

| | | |
|---|---|---|
| *A61K 31/405* | (2006.01) | |
| *A61K 31/675* | (2006.01) | |
| *A61P 21/00* | (2006.01) | |

(58) Field of Classification Search
CPC ........ A61K 31/704; A61P 39/00; A61P 43/00; A61P 9/00
See application file for complete search history.

(56) References Cited

FOREIGN PATENT DOCUMENTS

| | | | |
|---|---|---|---|
| CN | 105451578 | A | 3/2016 |
| CN | 108024983 | A | 5/2018 |
| JP | 2008510494 | A | 4/2008 |
| JP | 2013515718 | A | 5/2013 |
| JP | 2019058140 | A | 4/2019 |
| WO | 2004026294 | A1 | 4/2004 |
| WO | 2012141316 | A1 | 10/2012 |
| WO | 2018091564 | A1 | 5/2018 |
| WO | 2019035953 | | 2/2019 |
| WO | 2019090061 | | 5/2019 |
| WO | 2020018911 | A1 | 1/2020 |

OTHER PUBLICATIONS

Olza et al. "A specific protein-enriched enteral formula decreases cortisolemia and improves plasma albumin and amino acid concentrations in elderly patients" Nutrition & Metabolism, 2010, vol. 7, No. 58, 8 pages.

Aytekin et al., "Selected B Vitamins and their Possible Link to the Aetiology of Age-related Sarcopenia: Relevance Of UK Dietary Recommendations", Nutrition research reviews, vol. 31, 2018, pp. 204-224.

Japanese Office Action for Appl No. 2022-552639 dated Feb. 25, 2025, 6 pages.

Chinese Office Action for Appl No. 202180019809.7 dated Dec. 12, 2023.

Japanese Office Action for Appl No. 2022-552639 dated Nov. 18, 2025, 4 pages.

* cited by examiner

COMPOSITIONS CONTAINING AMINO ACIDS AND METHODS OF USING SUCH COMPOSITIONS FOR TREATING SARCOPENIA

CROSS REFERENCE TO RELATED APPLICATIONS

The present application is a National Stage of International Application No. PCT/EP2021/058555, filed on Apr. 1, 2021, which claims priority to U.S. Provisional Patent Application No. 63/003,495, filed on Apr. 1, 2020, the entire contents of which are being incorporated herein by reference.

TECHNICAL FIELD

The present disclosure generally relates to compositions containing one or more aromatic amino acids and also relates to methods of preparing and using such compositions. The compositions may further comprise vitamin B6 in an amount effective to increase the functional Vitamin B6, which is defined as the ratio of hydroxy-kynurenine (HK)/ xanthurenic acid (XA), a substrate: product pair of the kynurenine aminotransferase catalyzed by Vitamin B6.

BACKGROUND

Sarcopenia, or the decline of skeletal muscle tissue with age, is one of the most important causes of functional decline and loss of independence in older adults. Sarcopenia has been defined as an age related, involuntary loss of skeletal muscle mass and strength. Beginning as early as the 4th decade of life, evidence suggests that skeletal muscle mass and skeletal muscle strength decline in a linear fashion, with up to 50% of mass being lost by the 8th decade of life. Given that muscle mass accounts for about 40% of body mass, pathological changes to this important metabolically active tissue can have profound consequences on the older adult. The consequences of sarcopenia are often severe in older adults, as the strength and functional declines associated with sarcopenia can in turn contribute to a number of adverse health outcomes, including loss of function, disability, frailty and potentially loss of autonomy. Sarcopenia is also associated with acute and chronic disease states, increased insulin resistance, fatigue, falls, and mortality. Of the chronic disease states, sarcopenia has been associated with rheumatologic conditions, especially rheumatoid arthritis (RA) in women, among many other diseases.

Sarcopenia is a multi-factorial syndrome which associates with pathophysiological changes, such as impaired neuro-muscular transition, altered excitation/contraction coupling, impaired regenerative capacity linked to stem cell exhaustion, defects of mitochondrial and energy metabolism in myofibers, and marbling of skeletal muscle with fat and fibrosis. The aetiology of this syndrome is therefore complex and poorly understood, but low physical activity, hormonal decline in anabolic hormones (e.g. androgens and IGF-1), and malnutrition and/or nutritional deficiencies play an important role.

The physiological and morphological changes in skeletal muscle with advancing age are characterized by overall declines in size and number of skeletal muscle fibers, mainly the type 2 or fast-twitch muscle fibers, and a marked infiltration of fibrous and adipose tissue into the skeletal muscle.

Although aging-related biological changes clearly drive sarcopenia, it is increasingly clear that other factors such as inactivity due to injuries or sickness, obesity and fat infiltration into skeletal muscle also cause lower muscle quality and an accelerated loss of lean body mass.

Reduced physical activity is thought to increase the likelihood of sarcopenia and therefore increased exercise will likely be beneficial in combating the condition. Indeed, resistance exercise is associated with increased synthesis of proteins in skeletal muscle. However, exercise as a treatment often suffers from poor patient compliance.

There are currently no pharmacological agents approved for the treatment of sarcopenia. A number of growth hormones have been studied in this context, however these have shown little effect. In addition, anabolic steroids may increase muscle mass and strength, but are associated with a number of side effects, such as increased risk of prostate cancer.

The present inventors identified that there is an increasing demand for a solution for preventing and/or treating the loss of skeletal muscle mass, lean muscle mass, the skeletal muscle strength and/or the skeletal muscle function in an individual in need thereof, for example, treating sarcopenia in elderly adults; and an increasing demand for improving the skeletal muscle mass, the skeleton lean muscle mass, the skeletal muscle strength and/or the skeletal muscle function in an individual in need thereof.

SUMMARY

As set forth in the experimental examples disclosed later herein, the present inventors surprisingly found that muscle losses and/or loss of muscle function was strongly associated with the low concentration of specific nutrients (especially some amino acids and vitamin B6) and suggest that a composition comprising a combination of amino acids, particularly at specific concentrations and/or specific ratios thereof, could be used to improve the skeletal muscle mass, the skeleton lean muscle mass, the skeletal muscle strength and/or the skeletal muscle function in an individual in need thereof. The present inventors also surprisingly found that the composition was advantageous in preventing and/or treating a loss of skeletal muscle mass, skeleton lean muscle mass, skeletal muscle strength and/or skeletal muscle function for a variety of reasons such as aging, obesity, and inactivity due to injuries or sickness, for example for treating sarcopenia in an elderly adult. Moreover, the present inventors surprisingly found that there is a statistically significant synergistic association between the low concentration of different amino acids and functional Vitamin B6 and the loss of muscle mass and/or function, thus suggesting a preventing and/or treating effect of these nutrients on the loss of and/or improving skeletal muscle mass, skeleton lean muscle mass, skeletal muscle grip strength and/or skeletal muscle function in an individual in need thereof, such as treating sarcopenia in an elderly adult.

As set forth in the experimental examples disclosed later herein, a combination of vitamin B6 and one or more amino acids (e.g., one or more aromatic amino acids, such as tryptophan (Trp), tyrosine (Tyr), phenylalanine (Phe) and/or histidine (His)), particularly at specific concentrations and/ or specific ratios thereof, unexpectedly showed a statistically significant synergistic association between the low concentration of different amino acids and Vitamin B6 and the loss of muscle mass and/or function, thus suggesting an effect of these nutrients on preventing and/or treating the loss of and/or improving skeletal muscle mass, skeleton lean muscle mass, skeletal muscle strength and/or skeletal muscle function in an individual in need thereof, especially for treating sarcopenia in an elderly adult.

In an aspect of the present disclosure, a composition comprises one or more amino acids, preferably one or more aromatic amino acids, and preferably a total amount of the one or more amino acids that is therapeutically effective for at least one of the physiological benefits disclosed herein. In an embodiment, the composition further comprises vitamin B6, in an amount effective to increase the functional Vitamin B6 which is defined as the ratio of hydroxy-kynurenine (HK)/xanthurenic acid (XA), a substrate: product pair of the kynurenine aminotransferase catalyzed by Vitamin B6. The composition can comprise the vitamin B6 in an amount of 1.0-12.0 mg/300 Kcal energy and/or a daily dosage of 1.0-25.0 mg of the vitamin B6/day. In an embodiment, the composition comprises the one or more aromatic amino acids in a daily dosage of 0.5-20.0 g of the one or more aromatic amino acids/day.

In another aspect of the present disclosure, a composition comprises a combination of vitamin B6 and one or more aromatic amino acids, preferably an amount of the combination that is therapeutically effective for at least one of the physiological benefits disclosed herein. Preferably the vitamin B6 is provided in an amount effective to increase the functional Vitamin B6 (which is defined as the ratio of hydroxy-kynurenine (HK)/xanthurenic acid (XA), a substrate: product pair of the kynurenine aminotransferase catalyzed by Vitamin B6). In an embodiment, the one or more aromatic amino acids are selected from the group consisting of Trp, Phe, Tyr, His. In an embodiment, the composition further comprises at least one of EAAs, an/or BCAAs, e.g. lysine (Lys), methionine (Met), leucine (Leu), valine (Val), threonine (Thr), a combination of essential amino acids (EAAs), and a combination of branched chain amino acids (BCAAs).

In an embodiment, the composition comprises vitamin B6 in an amount of 1.0-12.0 mg of vitamin B6/300 Kcal energy and/or a daily dosage of 1.0-25.0 mg of vitamin B6/day. The composition can comprise the one or more amino acids in a total daily dosage of 0.5-20.0 g of the one or more aromatic amino acids/day.

In an embodiment, the composition comprises a combination of vitamin B6 in an effective amount to increase the functional Vitamin B6, and a plurality of aromatic amino acids, preferably an amount of the combination that is therapeutically effective for at least one of the physiological benefits disclosed herein. The plurality of aromatic amino acids may include at least Trp, Tyr, Phe and His. The composition can comprise a total daily dosage of the plurality of aromatic amino acids in the composition that can be 0.5-20.0 g of the plurality of aromatic amino acids/day, preferably 3.0-20.0 g/day. In an embodiment, the composition comprises at least one formulation selected from the group consisting of (i) vitamin B6 and Trp, (ii) vitamin B6 and Tyr, (iii) vitamin B6 and Phe, (iv) vitamin B6 and Thre, (v) vitamin B6 and Met, (vi) vitamin B6 and Lys and (vii) vitamin B6 and a plurality of essential amino acids (EAA), wherein Vit B6 is provided in an effective amount to increase the functional Vitamin B6.

In an embodiment, the composition is in a form of a solid powder, a powdered stick, a capsule or a solution. The composition can be a food supplement, a medical food, a nutritional composition, for example an oral nutritional composition.

In another aspect of the present disclosure, a method of preparing the composition is provided. The method can comprise combining vitamin B6 and one or more amino acids, and preferably an amount of the resultant combination that is therapeutically effective for at least one of the physiological benefits disclosed herein.

In another aspect of the present disclosure, a nutritional supplement comprises a therapeutically effective amount of any of the compositions disclosed herein. In an embodiment, the nutritional supplement is an oral nutritional supplement (ONS). The nutritional supplement can be in a form of a solid powder, a powdered stick, a capsule, or a solution. In an embodiment, the nutritional supplement comprises vitamin B6 in an amount effective to increase functional Vit B6, in the supplement in an amount of 1.0-6.0 mg of the vitamin B6/300 Kcal energy and/or a daily dosage of 1.0-25 mg of vitamin B6/The nutritional supplement can comprise the one or more amino acids in a total daily dosage of 0.5-20.0 g of the one or more aromatic amino acids/day.

In another aspect of the present disclosure, a food product comprises any of the compositions disclosed herein. In an embodiment, the food product is a food for special medical purpose (FSMP). The food product can comprise vitamin B6 in the food product in an amount effective to increase the functional Vitamin B6, preferably in an amount of 1.0-6.0 mg of vitamin B6/300 Kcal energy and/or a daily dosage of 1.0-25 mg of vitamin B6. In an embodiment, the food product comprises the one or more amino acids in the food product in a total daily dosage of 0.5-20.0 g of the one or more aromatic amino acids/day.

In an embodiment, the food product further comprises one or more additional ingredients, for example a lipid, a protein, a carbohydrate, a vitamin, a mineral, or any combination thereof.

In another aspect of the present disclosure, a kit comprises a therapeutically effective amount of any of the compositions disclosed herein. In an embodiment, the kit is configured for oral administration of the composition. For example, the kit can comprise at least two capsules in which a first capsule comprises the vitamin B6 (preferably functional vitamin B6) and a second capsule comprises the one or more amino acids. In an embodiment, the kit comprises vitamin B6 in the first capsule in an amount of 1.0-6.0 mg of the vitamin B6/300 Kcal energy and/or and a daily dosage of 1.0-25 mg of the vitamin B6. In an embodiment, the kit comprises the one or more amino acids in the second capsule in a total daily dosage of 0.5-20.0 g of the one or more aromatic amino acids/day.

In another aspect of the present disclosure, a method of preventing and/or treating a loss of and/or improving skeletal muscle mass, skeleton lean muscle mass, skeletal muscle grip strength and/or skeletal muscle function is provided. The method comprises administering to an individual in need thereof a therapeutically effective amount of a combination of vitamin B6 in an amount effective to increase the functional Vitamin B6 and one or more amino acids. In an embodiment, the administration is by oral administration. In another embodiment, the administration is by intravenous administration.

The present invention also relates to a method for treating or preventing sarcopenia and/or restoring and/or correcting deficiencies of nutrients in a subject. In one embodiment, the subject is identified as having sarcopenia or is at increased risk of developing sarcopenia.

In one embodiment, the subject is a human subject.

In one embodiment, the human subject is an older adult.

In one embodiment, the human subject is elderly.

In one embodiment, the subject is a companion animal, preferably a dog.

DETAILED DESCRIPTION

Definitions

Figure 1:
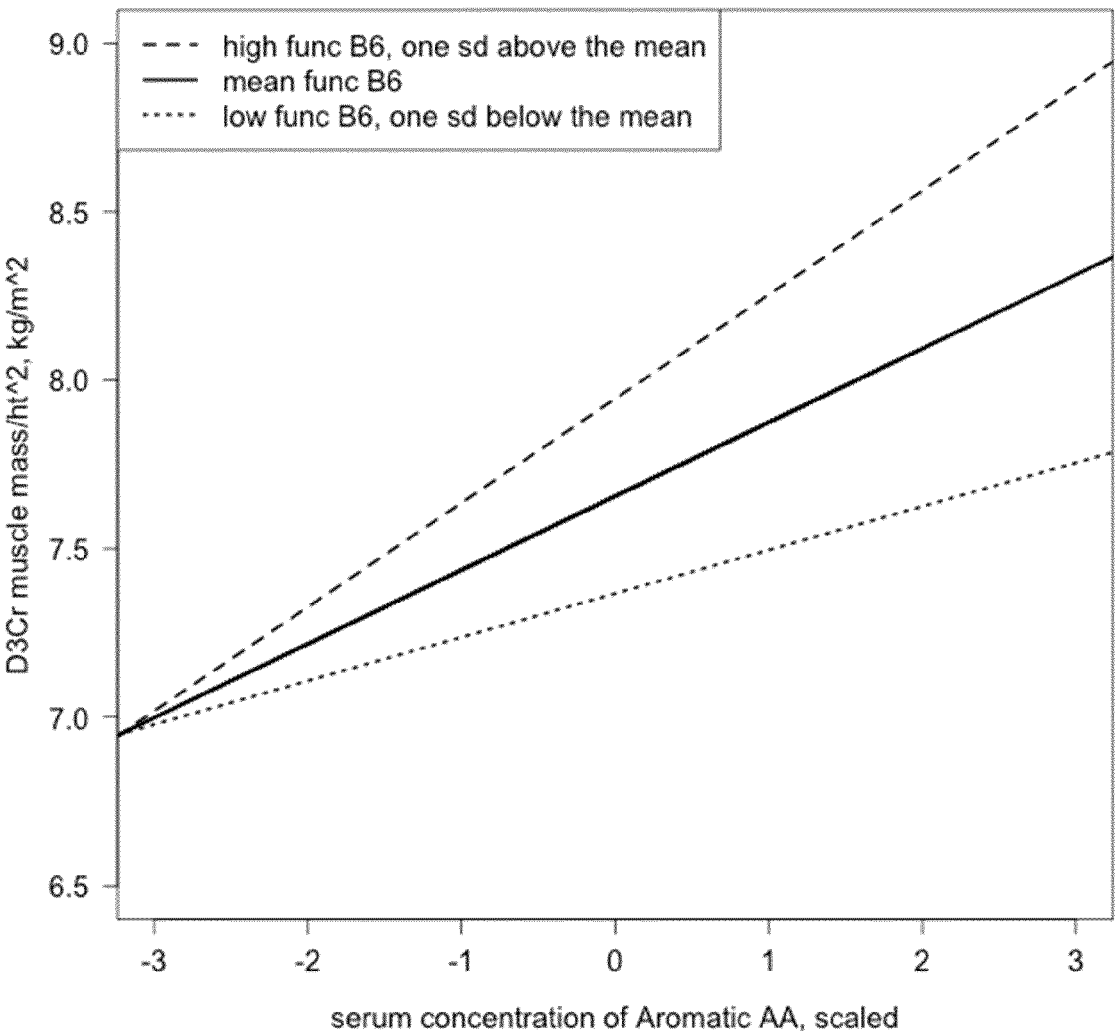
FIG. 1 shows the partial effects plot of association between muscle mass measured by the D3 creatine dilution method and the sum of the aromatic amino acid (AAA) concentrations in serum for different level of serum functional vitamin B6 (defined as the ratio of hydroxy-kynurenine (HK)/xanthurenic acid (XA)) at mean age. The interaction term between functional vitamin B6 and AAA is significant and indeed the lines representing the association between muscle mass and AAA concentration at constant age for increasing level of functional vitamin B6 have increasing slopes in Example 1 disclosed herein.

Some definitions are provided hereafter. Nevertheless, definitions may be located in the "Embodiments" section below, and the above header "Definitions" does not mean that such disclosures in the "Embodiments" section are not definitions.

All percentages expressed herein are by weight of the total weight of the composition unless expressed otherwise. When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example, "at least one of Trp or Phe" should be interpreted as "Trp," or "Phe," or "both Trp and Phe."

Where used herein, the terms "example" and "such as," particularly when followed by a listing of terms, are merely exemplary and illustrative and should not be deemed to be exclusive or comprehensive.

A "subject" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form," as used herein, refers to physically discrete units suitable as unitary dosages for human and animal subjects, each unit containing a predetermined quantity of the composition disclosed herein in an amount sufficient to produce the desired effect, in association with a therapeutically effective diluent, carrier or vehicle. The specifications for the unit dosage form depend on the particular compounds employed, the effect to be achieved, and the pharmacodynamics associated with each compound in the host.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

The term "food for special medical purpose (FSMP)" refers to formula foods specially processed and prepared in order to meet special needs for nutrient or diet of those suffering from food intake restriction, disorder of digestive absorption, disorder of metabolic or certain diseases. Such foods shall be used alone or together with other foods under the guidance of a doctor or clinical nutritionist. FSMP is a special dietary food, not medicine, but not ordinarily eaten by normal people. It is specially developed by clinicians and nutritionists based on scientific facts after extensive medical research.

The term "oral nutritional supplement (ONS)" refers to sterile liquids, semi-solids or powders, which provide macro and micro nutrients. They are widely used within the acute and community health settings for individuals who are unable to meet their nutritional requirements through oral diet alone.

The term "Dietary Reference Intakes (DRIs)" is a collective term intended for the general public and health professionals. DRIs comprise a set of at least four categories of nutrient-based reference values, such as the Recommended Dietary Allowance (RDA), Adequate Intake (AI), Tolerable Upper Intake Level (UL) and Estimated Average Requirement (EAR), each of which has special uses.

The term "Estimated Average Requirements (EAR)" refers to the intake level for a nutrient at which the needs of 50 percent of the population in that age group will be met. Because the needs of the other half of the population will not be met by this amount, the EAR is increased by about 20 percent to arrive at the Recommended Dietary Allowances (RDA).

The term "Recommended Dietary Allowances (RDA)" refers to the average daily dietary intake level of a nutrient considered sufficient by the Food and Nutrition Board of the Institute of Medicine to meet the requirements of 97.5% of healthy individuals in each life-stage and sex group. The definition implies that the intake level would cause a harmful nutrient deficiency in just 2.5%. It is calculated based on the EAR and is usually approximately 20% higher than the EAR.

The term "Recommended Dietary Intake (RDI)" or as recommended daily intake as used refers to the average daily intake level of a particular nutrient that is likely to meet the nutrient requirements of 97-98% of healthy individuals in a particular life stage or gender group.

The term "Adequate Intake (AI)" refers to, where no RDA or EAR has been established, the estimates of intake levels of healthy populations, but the amount established is somewhat less firmly believed to be adequate for everyone in the demographic group.

The term "Tolerable Upper Intake Levels (UL)" refers to the highest level of daily nutrient consumption that is considered to be safe for, and cause no side effects in, 97.5% of healthy individuals in each life-stage and sex group. The UL cautions against excessive intake of nutrients (like vitamin A) that can be harmful in large amounts. The definition implies that the intake level would cause a harmful nutrient excess in just 2.5%.

The term "Acceptable Macronutrient Distribution Ranges (AMDR)" refers to a range of intake specified as a percentage of total energy intake. The AMDR is used for sources of energy, such as fats and carbohydrates.

The term "amino acid" as used herein includes free form amino acids, amino acids in molecules between 2 and 20 amino acids (referenced herein as "peptides"), and also includes longer chains of amino acids as well. Small peptides, i.e., chains of 2 to 10 amino acids, are suitable for the composition alone or in combination with other proteins. The "free form" of an amino acid is the monomeric form of the amino acid.

Each amino acid disclosed herein can be present in the composition as only one type of the amino acid or as a mixture of one or more types of the amino acid, for example one or more (i) peptides containing the amino acid, (ii) longer chains of amino acids including the amino acid, or (iii) free form of the amino acid. For example, a disclosure of "a composition comprising an aromatic amino acid" constitutes a disclosure of aromatic amino acids only in free form, a disclosure of aromatic amino acids only bound to other amino acids, and a mixture of aromatic amino acids in free form and aromatic amino acids bound to other amino acids. In embodiments where the referenced amino acid is in free form, optionally the composition can have substantially no protein containing the referenced amino acid. Similarly, in embodiments where the referenced amino acid is in peptides, optionally the composition can have substantially no free form of the referenced amino acid.

The term "an essential amino acid (EAA)" or an indispensable amino acid as used means an amino acid that cannot be synthesized de novo by the organism at a rate commensurate with its demand, and thus must be supplied in its diet. Of the twenty one amino acids common to all life forms the following nine amino acids are considered essential amino acids in the human diet which include phenylalanine, valine, threonine, tryptophan, methionine, leucine, isoleucine, lysine and histidine. Six other amino acids which are considered conditionally essential in the human diet are arginine, cysteine, glycine, glutamine, proline and tyrosine. There are six amino acids are non-essential (dispensable) in human diet, and these six non-essential amino acids are alanine, aspartic acid, asparagine, glutamic acid, serine and selenocysteine.

The term "an aromatic amino acid (AAA)" refers to an amino acid that includes an aromatic ring. Examples of aromatic amino acids include: Phenylalanine (symbol Phe or F); Tryptophan (symbol Trp or W); Tyrosine (symbol Tyr or Y); and Histidine (symbol His or H).

The term "a branched chain amino acid (BCAA)" means an amino acid having an aliphatic side-chain with a branch (a central carbon atom bound to three or more carbon atoms). Among the proteinogenic amino acids, there are three BCAAs: leucine (Leu or L), isoleucine (Ile or I), and valine (Val or V). Non-proteinogenic BCAAs include 2-aminoisobutyric acid.

As used herein, "vitamin B6" can include one or more of the following: pyridoxine (PN), pyridoxal 5'-phosphate (PLP), pyridoxine 5'-phosphate (P5P), pyridoxal (PL), pyridoxamine (PM), pyridoxamine 5'-phosphate (PMP), 4-pyridoxic acid, and pyritinol. In a preferred embodiment, at least a portion of any vitamin B6 is PN. At least a portion of the vitamin B6 can be PLP. Absorbed pyridoxamine is converted to PMP by pyridoxal kinase, which is further converted to PLP by pyridoxamine-phosphate transaminase or pyridoxine 5'-phosphate oxidase which also catalyzes the conversion of PNP to PLP. [2] Pyridoxine 5'-phosphate oxidase is dependent on flavin mononucleotide (FMN) as a cofactor produced from riboflavin (vitamin B2). Functional B6 is defined as bioactive levels of PLP which are assessed by the ratio of hydroxy-kynurenine (HK)/xanthurenic acid (XA), a substrate: product pair of the kynurenine aminotransferase catalyzed by PLP As used herein, Sarcopenia is characterized by one or more of low muscle mass, low muscle strength, and low physical performance. More preferably, sarcopenia is characterized by two or more of low muscle mass, low muscle strength, and low physical performance. Most preferably, sarcopenia is characterized by low muscle mass, low muscle strength, and low physical performance. These can all be measured by methods well known to the person skilled in the art.

Muscle mass can be measured by CT (computerised tomography), DXA (Dual-energy X-ray absorptiometry), MRI (Magnetic Resonance Imaging) or D3 creatine dilution methods.

Muscle strength can be measured by handgrip strength (for example, using hand held dynamometry) or knee extensor strength (for example, using quadriceps torque measurement).

Physical performance can be measured by gait speed, SPPB, 400 m walk test, time up and go test, or stair climbing test.

Sarcopenia can be diagnosed in a subject based on the definition of the AWGSOP (Asian Working Group for Sarcopenia in Older People), for example as described in Chen, et al. (2014) "Sarcopenia in Asia: consensus report of the Asian Working Group for Sarcopenia" Journal of the American Medical Directors Association 15, 95-101. Low muscle mass can generally be based on low appendicular lean mass normalized to height square (ALM index), particularly ALM index less than 7.00 kg/m2 for men and 5.40 kg/m2 for women. Low physical performance can generally be based on gait speed, particularly gait speed of <0.8 m/sec. Low muscle strength can generally be based on low hand grip strength, particularly hand grip strength less than 26 kg in men and less than 18 kg in women.

Sarcopenia can be diagnosed in a subject based on the definition of the EWGSOP (European Working Group for Sarcopenia in Older People), for example as described in Cruz-Jentoft et al., 2010 "Sarcopenia: European consensus on definition and diagnosis: Report of the European Working Group on Sarcopenia in Older People" Age Ageing 39, 412-423. Low muscle mass can generally be based on low appendicular lean mass normalized to height square (ALM index), particularly ALM index less than 7.23 kg/m2 for men and 5.67 kg/m2 for women. Low physical performance can generally be based on gait speed, particularly gait speed of <0.8 m/sec. Low muscle strength can generally be based on low hand grip strength, particularly hand grip strength less than 30 kg in men and less than 20 kg in women.

Sarcopenia can be diagnosed in a subject based on the definition of the Foundation for the National Institutes of Health (FNIH), for example as described in Studenski et al., 2014 "The FNIH sarcopenia project: rationale, study description, conference recommendations, and final estimates, J Gerontol A Biol Sci Med Sci. 69(5), 547-558. Low muscle mass can generally be based on low appendicular lean mass (ALM) normalized to body mass index (BMI; kg/m2), particularly ALM to BMI less than 0.789 for men and 0.512 for women. Low physical performance can generally be based on gait speed, particularly gait speed of <0.8 m/sec. Low muscle strength can generally be based on low hand grip strength, particularly hand grip strength less than 26 kg in men and less than 16 kg in women. Low muscle strength can also generally be based on low hand grip strength to body mass index, particularly hand grip strength to body mass index less than 1.00 in men and less than 0.56 in women.

The D3-creatine dilution method is another approach to measure muscle mass. This method is becoming more widely accepted as a robust standard and potentially a future alternative to DXA. The D3-creatine dilution method has been described previously e.g. in Clark et al. (2014) "Total body skeletal muscle mass: estimation by creatine (methyl-d3) dilution in humans" J Appl Physiol (1985). 2014 Jun. 15; 116(12):1605-13 and Stimpson et al. (2013) "Longitudinal changes in total body creatine pool size and skeletal muscle mass using the D3-creatine dilution method" J Cachexia Sarcopenia Muscle. June 25.

Embodiments

An aspect of the present disclosure is a composition comprising one or more aromatic amino acids, particularly at specific concentrations and/or specific ratios thereof. In an embodiment, the amino acid is selected from the group consisting of Trp, Phe, Tyr, His, a combination of aromatic amino acids. The composition comprising the one or more aromatic amino acids is advantageous in preventing and/or treating the loss of and/or improving skeletal muscle mass, skeleton lean muscle mass, skeletal muscle strength and/or skeletal muscle function for a variety of reasons such as aging and inactivity due to injuries or sickness, for example for treating sarcopenia in an elderly adult.

Non-limiting examples of the one or more amino acids include Trp, Phe, Tyr, His and combinations thereof. In an embodiment, the composition comprises the one or more amino acids in a total daily dosage of 0.5-20.0 g of the one or more amino acids/day.

Non-limiting examples of the composition comprise a single amino acid. For example, the single amino acid can be one of the aromatic amino acids: Trp, Phe, Tyr and His.

In an embodiment, the composition further comprises vitamin B6, in an amount to increase the functional Vitamin B6 (which is defined as the ratio of hydroxy-kynurenine (HK)/xanthurenic acid (XA), a substrate: product pair of the kynurenine aminotransferase catalyzed by Vitamin B6), for example vitamin B6 in an amount of 1.0-12.0 mg of the vitamin B6/300 Kcal energy and/or a daily dosage of 1.0-25.0 mg of the vitamin B6/day.

In another aspect of the present disclosure, the composition comprises a therapeutically effective amount of a combination of vitamin B6 in an amount effective to increase the functional Vitamin B6, and a plurality of aromatic amino acids, preferably an amount therapeutically effective for at least one of the physiological benefits disclosed herein. The plurality of aromatic amino acids may include at least Trp, Tyr, Phe and His. For example, the composition can comprise at least one formulation selected from the group consisting of (i) vitamin B6 and Trp, (ii) vitamin B6 and Tyr, (iii) vitamin B6 and Phe, and (iv) vitamin B6 and His.

The composition can be a nutritional composition, for example an oral nutritional composition.

Another aspect of the present disclosure is a method of preparing the composition. The method can comprise combining a therapeutically effective amount of a combination of aromatic amino acids and vitamin B6 and one or more of essential amino acids (EAAs), one or more of branched chain amino acids BCAAs, preferably an amount of the combination that is therapeutically effective for at least one of the physiological benefits disclosed herein.

Another aspect of the present disclosure is a nutritional supplement comprising a therapeutically effective amount of any of the compositions disclosed herein, for example an oral nutritional supplement. The nutritional supplement can be in a form of a solid powder, a powdered stick, a capsule, or a solution. Preferably the nutritional supplement comprises vitamin B6 in the supplement in an amount effective to increase the functional Vitamin B6, preferably in an amount of 1.0-12.0 mg of vitamin B6/300 Kcal energy and/or a daily dosage of 1.0-25.0 mg of vitamin B6/day. In an embodiment, the nutritional supplement comprises the one or more amino acids in a total daily dosage of 0.5-20.0 g of the one or more aromatic amino acids/day.

Another aspect of the present disclosure is a capsule comprising any of the compositions disclosed herein, for example the composition comprising vitamin B6 and one or more aromatic amino acids. In an embodiment, the capsule comprises a therapeutically effective amount of a combination of vitamin B6 in an amount effective to increase the functional Vitamin B6, and one or more aromatic amino acids, and preferably the one or more amino acids are selected from the group of Trp, Phe, Tyr, His, and a combination of all aromatic amino acids (AAAs). In one embodiment, the capsule comprises vitamin B6 (e.g., functional vitamin B6) in an amount of 1.0-25.0 of the vitamin B6 mg per capsule, or preferably 5.0-10.0 mg of the vitamin B6 per capsule.

In an embodiment, the capsule comprises a combination of vitamin B6 and Trp (e.g., a combination of functional vitamin B6 and Trp). For example, the vitamin B6 in the capsule can be 1.0-7.0 mg per capsule, preferably about 6.7 mg/capsule. The Trp in the capsule can be 0.1-1.0 g/capsule, preferably about 0.5 g/capsule.

In another embodiment, the capsule comprises a combination of vitamin B6 and Tyr (e.g., functional vitamin B6 and Tyr). For example, the Tyr in the capsule can be 0.1-2.0 g/capsule, preferably about 1.0 g/capsule.

In another embodiment, the capsule comprises a combination of vitamin B6 and Phe (e.g., functional vitamin B6 and Phe). For example, the Phe in the capsule can be 0.05-1.5 g/capsule, preferably about 1.0 g/capsule.

In another embodiment, the capsule comprises a combination of vitamin B6 and His (e.g., functional vitamin B6 and His). For example, the His in the capsule can be 0.1-1.5 g/capsule, preferably 0.5-1.5 g/capsule.

Another aspect of the present disclosure is a food product comprising any of the compositions disclosed herein, for example a food for special medical purpose (FSMP). The composition can comprise a combination of vitamin B6 (in an amount effective to increase the functional Vitamin B6) and one or more aromatic amino acids. The one or more aromatic amino acids can be selected from the group consisting of Trp, Phe, Tyr, His and a combination of aromatic amino acids. In an embodiment, the vitamin B6 is present in the FSMP in an amount of about 0.1-about 0.5 mg of the vitamin B6/100 Kcal energy, preferably about 0.50 mg of the vitamin B6/100 Kcal. In an embodiment, the one or more amino acids are present in the FSMP in a total amount of 0.1-5.0 g of the one or more amino acids/day.

In an embodiment of the FSMP, the one or more aromatic amino acids comprise Trp. The daily dosage of the Trp in the FSMP can be 0.5-2.0 g/day, preferably 0.8-1.2 g/day. In an embodiment, the one or more amino acids comprise Tyr. The daily dosage of the Tyr in the FSMP can be 1.0-6.0 g/day, preferably about 2.8 g/day. In an embodiment, the one or more amino acids comprise Phe. The daily dosage of the Phe in the FSMP can be 1.0-6.0 g/day, preferably about 4.7 g/day. In an embodiment, the one or more amino acids comprise His. The daily dosage of the His in the FSMP can be 1.0-4.0 g/day, preferably about 1.6 g/day. In an embodiment, the one or more amino acids comprise a combination of aromatic amino acids (AAAs). The daily dosage of the total amount of the AAAs in the FSMP can be 2.0-20 g/day, preferably 9.0-11.0 g/day.

Another aspect of the present disclosure is a kit comprising a therapeutically effective amount of any of the compositions disclosed herein. In an embodiment, the kit is configured for oral administration of the composition. For example, the kit can be in a form of two capsules, wherein the first capsule comprises the vitamin B6 in an amount effective to increase the functional Vitamin B6, and the second capsule comprises the one or more aromatic amino acids. The one or more aromatic amino acids can be selected from the group consisting of Trp, Phe, Tyr, His and combinations thereof.

Another aspect of the present disclosure is a method of preventing and/or treating a loss of and/or improving skeletal muscle mass, skeleton lean muscle mass, skeletal muscle grip strength and/or skeletal muscle function. The method comprises administering to an individual in need thereof a therapeutically effective amount of any of the compositions disclosed herein. Non-limiting examples of the administration include oral administration and intravenous administration. In an embodiment, the administration is oral administration. In an embodiment, the method comprises administering to an individual in need thereof a therapeutically effective amount of a combination of vitamin B6 and one or more amino acids.

In another embodiment, the method comprises administering to an individual in need thereof a therapeutically effective amount of a combination of vitamin B6 in an amount effective to increase the functional Vitamin B6, at least one aromatic amino acid and one or more EAAs and/or BCAAs. In an embodiment, the one or more amino acids are selected from the group consisting of consisting of Lys, Met, Thr, Leu, Ile, Val, a combination of aromatic amino acids (AAAs), a combination of essential amino acids (EAAS), a combination of branched chain amino acids (BCAAs), and combinations thereof.

In an embodiment, the method comprises administering to an individual in need thereof a therapeutically effective amount of a combination of vitamin B6 in an amount effective to increase the functional Vitamin B6, and one or more aromatic amino acids. The one or more aromatic amino acids can be selected from the group consisting of Trp, Phe, Tyr, His and combinations thereof. In an embodiment, the one or more amino acids is a combination of all aromatic amino acids (AAAs), and the dosage of the total AAAs is 3.0 to 20.0 g/day. The daily dosages of Trp, Tyr, Phe and His can be 0.2-3.0 g/day, 1.5-8.8 g/day, 1.5-10.7 g/day and 0.9-5.6 g/day respectively.

In an embodiment, the daily dosage of vitamin B6 is 1.0-12.0 mg/300 Kcal or 1.0-25.0 mg/day, and/or the daily dosage of vitamin B6 is 1.0-12.0 mg/300 Kcal or 1.0-25.0 mg/day.

In an embodiment, the method comprises administering to an individual in need thereof a therapeutically effective amount of a combination of vitamin B6 in an amount effective to increase the functional Vitamin B6, and a single aromatic amino acid. The single aromatic amino acid can be selected from the group consisting of Trp, Phe, Tyr and His. In an embodiment, the single aromatic amino acid is Trp, and the daily dosage of the Trp can be 0.2-3.0 g/day. In an embodiment, the single aromatic amino acid is Tyr, and the daily dosage of Tyr can be 1.5-8.8 g/day. In an embodiment, the single aromatic amino acid is Phe, and the daily dosage of Phe can be 1.5-10.7 g/day. In an embodiment, the single aromatic amino acid is His, and the daily dosage of His can be 1.0-5.6 g/day.

In an embodiment, the method comprises administering to an individual in need thereof a therapeutically effective amount of a combination of vitamin B6 and Met.

In another embodiment, the method comprises administering to an individual in need thereof a therapeutically effective amount of a combination of vitamin B6 and Lys.

In another embodiment, the method comprises administering to an individual in need thereof a supplement comprising a therapeutically effective amount of any of the compositions disclosed herein.

In another embodiment, the method comprises administering to an individual in need thereof a food product comprising a therapeutically effective amount of any of the compositions disclosed herein.

In an embodiment, the method comprises providing a kit to an individual in need thereof, wherein the kit comprising a therapeutically effective amount of a combination of vitamin B6 in an amount effective to increase the functional Vitamin B6, and one or more amino acids. For example, the kit is preferably configured for oral administration. In an embodiment, the kit comprises two capsules, wherein the first capsule contains the vitamin B6 and the second capsule contains the one or more amino acids.

Preferred daily dosages for oral administration of each of the components in the compositions, the supplements, the food products and the kits disclosed in the present disclosure can be as follows:

For example, for a supplement in capsule,

Vitamin B6: 50 mg per capsule and 1-2 capsules per day: up to 100 mg/day

Tryptophan: Trp+VitB6: 6.7 mg B6-1 g Trp with 2 capsule-Up to 6 capsules=20.1 g B6 and 3 g Trp Tyrosine: 1 capsule 1 g up to 4 capsules=4 g Phenylalanine: Phe 1 g/capsule up to 4 capsules/day=4 g/d BCAA capsule: 2 capsules=1.2 g BCAA=600 mg Leu-300 mg Ileu-300 mg Val-Up to 2 capsules=2.4 g BCAA BCAA powder: 3 g BCAA=1500 mg Leu+750 mg Ileu+750 mg Val EAA: Complete list of EAA but low level As another example, for an Oral Nutritional Supplement (ONS) product where 1 serving=200 ml and 300 Kcal, Vitamin B6: 1.1 mg/200 ml in 2 serving Tryptophan: 0.5 g/2 serving/d+food intake=1.5 g/d Tyrosine: 0.39 g/100 g thus 1.6 g/2 serving/d Phenylalanine: 0.41 g/100 g thus 1.6 g/2 serving Histidine: 0.23 g/100 g thus 0.9 g/2 serving/d As another example, for a general product, Vitamin B6: 1-12 mg/300 kcal/serving Tryptophan: 0.5 to 2 g/2 servings thus total food intake of 1.5-3 g/d Tyrosine: 1.5 to 6 g/2 servings thus total food intake of 4.3 to 8.8 g/d Phenylalanine: 1.5 to 6 g/2 servings thus total food intake up to 10.7 g/d Histidine: 1 to 4 g/2 servings thus total food intake up to 5.6 g/d Total aromatic AA: Max dose: 20 g/day (the sum of individual AA)

EXAMPLES

The following non-limiting examples support the unexpected effectiveness of a composition comprising aromatic amino acids and optionally further comprising vitamin B6 for preventing and/or treating the loss of skeletal muscle mass, muscle strength and/or muscle function.

Example 1

A study investigated the synergistic effects between vitamin B6 or functional vitamin B6 and different amino acids.

Participant Selection: From 2000-2002, 5,994 ambulatory community-dwelling men aged ≥65 years without bilateral hip replacements were enrolled in the MrOS, a multicenter cohort study of aging and osteoporosis. The study was approved by the Institutional Review Board at each participating center and all participants provided written informed consent. In 2014-2016, 2,786 survivors were contacted to participate in a follow-up clinic visit.

529 participants were selected based on random sampling in the cohort or enrichment of physical disability based on low grip strength, low walking speed, low lean mass by DXA (ALM/ht$^2$), and low muscle mass measured by D3 creatine dilution (D$_3$Cr/weight). Participants with stroke or Parkinson's disease, those taking oral corticosteroids, and those on androgen depravation therapy were not eligible for inclusion in analyses.

Measures: Grip strength (kg) was assessed by analysing the maximal value from two tests of each hand using Jamar handheld dynamometers. Walking speed (m/s) was determined by timing completion of a 6-meter course at the participant's usual pace and taking the average of two trials. Skeletal muscle mass was estimated using D$_3$-creatine dilution methods described above. To account for variations in total muscle mass by body size, D$_3$Cr muscle mass was divided by height squared. Appendicular lean mass (ALM) was assessed by whole-body DXA scans (Hologic 4500 scanners, Waltham, MA). To account for body size differences, ALM was divided by height squared.

Vitamin B6 and kynurenines: Pyridoxal 5'-phosphate, 3-Hydroxykynurenine, Xanthurenic acid were measured with LC-MS/MS. Measurements were performed by mixing serum samples with labelled internal standards and resolving the analytes on a C8 liquid chromatography column by a gradient-type mobile phase, and detected using electrospray ionization tandem mass spectrometry as described in Midttun 2009.

Amino acids: Aromatic amino acids (Phenylalanine, Tyrosine, Tryptophan, Histidine) and branched chain amino acids (Valine, Isoleucine, Leucine), were measured in serum by ultra-performance liquid chromatography tandem mass spectrometry (UPLC-MS/MS).

Briefly, 50 µl samples were precipitated with 10 µl of internal standards and 140 µl of MeOH+0.1% formic acid, then derivatized with borate buffer pH 8.8 and derivatization reagent followed by a dilution 1:50 in Ammonium formate 0.55 g/L in water at 0.1% FA. An Acquity UPLC System Waters (Milford, MA, USA) is used to inject 10 µl of sample via Waters AccQtag Ultra C18 1.7 µm 2.1×100 mm column into a TQ-XS Waters (Milford, MA, USA) mass spectrometer equipped with ESI+ source, with 1.5 kV capillary voltage, 600° C. desolvation temperature: 1000 L/h desolvation flow, 250 L/h cone flow, 7.0 Bar nitrogen nebulizer and 120° C. source temperature. Cone voltage and collision energy (Argon) were adjusted for each amino acid independently.

Statistical Analyses

The present inventors fitted multiple linear regression models as described by Equation 1 and 2.

$$y = c0 + c1*age + c2*vitB6 + c3*aa + \varepsilon \qquad \text{Equation 1}$$

$$y = c0 + c1*age + c2*vitB6 + c3*aa + c4*vitB6:aa + \varepsilon \qquad \text{Equation 2}$$

where y is a measure of muscle mass (D3 Creatine/height2), or gait speed or grip strength; age is the age at the time of the blood measurements; vitB6 is the functional vitamin B6 estimated as the ratio between Xanthurenic Acid and Hydroxykynurenine; aa is the sum of the aromatic amino acids (AromAA) or one of the aromatic amino acids (Trp, Phe, Tyr, His) or one of the branched chain amino acids (Leu, Ile, Val); $\varepsilon$ is the normally distributed error with mean 0. All nutrients were log-transformed and scaled, and age was scaled.

The present inventors tested if the model represented by Equation 2 including an interaction term between the vitamin B6 and one amino acid (or the sum of a group of amino acids) of interest better fit the experimental data than the simpler model represented by Equation 1 with no interaction term, in other words if the effect of vitamin B6 and an amino acid of interest is non additive, i.e. the coefficient of the interaction term is different from 0 and therefore the effect of an amino acid on the response variable is different according to the level of the vitamin B6 (as well as the effect of the vitamin B6 on the response variable is different according to the level of the amino acid of interest). Specifically, the present inventors tested if the interaction term c4 was not different from to 0, i.e if the effect of vitamin B6 and an amino acid of interest was additive (c4 not significantly different from 0), or alternatively if the interaction between vitamin B6 and an amino acid of interest was synergistic with the effect of an amino acid modified according to the level of the vitamin B6 (c4 significantly different from 0).

Results

The present inventors conducted experimental study and reported the likelihood ratio test comparing the two models represented by Equation 1 and 2 in Tables 2-4 below. The likelihood ratio test compares the likelihood of two models here represented by Equations 1 and 2 and allows to reject the simpler model without interaction term if the more complex model fit the data significantly better (likelihood ratio test p-value <0.1), implying that the interaction term is relevant.

Non additive or synergy: If the model represented by Equation 1 is rejected and the model represented by Equation 2 is retained, likelihood ratio test p-value <0.1, and the sign of the interaction coefficient c4 is positive, then the combination of the two components increases muscle mass, muscle strength and/or muscle function in an individual in need thereof of one or both components, at higher levels than the components alone or the additive effects of each of the two components alone. Specifically, when the combination of the two components, vitamin B6 and an amino acid, result in a positive interaction coefficient c4 with a P-value less than 0.1, then the combination of the two components increases muscle mass, muscle strength and/or muscle function in an individual in need thereof of one or both components, at higher levels than the components alone or the additive effects of each of the two components alone.

Additive or indifference: If the model represented by Equation 1 is not rejected, i.e. is retained, likelihood ratio test p-value >0.1, then the combination has no significant increase in muscle mass, muscle strength and/or muscle function in an individual in need thereof, from the additive effect of each of the two components alone. Specifically, when the combination of the two components results in a P-value greater than 0.1 for the interaction coefficient c4, the combination has no significant increase in muscle mass, muscle function, muscle strength and/or physical performance in an individual in need thereof, from the additive effect of each of the two components alone.

Antagonism: When the combination of components results in a negative interaction coefficient c4 with a P-value less than 0.1 the combination of two components lowers the effectiveness of one or both of the two components alone.

Tables 2-4 below show the likelihood ratio tests for multiple regression models with and without interaction term between functional vitamin B6 and an amino acid for the following outcome variables: muscle mass (D3 Creatine/height^2); lean muscle mass (ALM/height^2); gait speed; and muscle grip strength respectively. In both models, the present inventors surprisingly found that the test results clearly demonstrated a synergistic effect between the functional vitamin B6 and one of or a combination of the aromatic amino acids (P-value <0.1). The P-value lower than 0.1 indicates the existence of synergistic effects between the components, and the lower the P-value indicates the strongest synergistic effects between the two components.

Specifically, the combination of the functional vitamin B6 with aromatic amino acids result in a P-value of 0.0175 in the outcome variable of muscle mass (D3Creatine/height^2); a P-value of 0.0342 in the outcome variable of gait speed; and a P-value of 0.0316 in the outcome variable of grip strength, as shown in Tables 2-4. These test results clearly demonstrated that the combination of vitamin B6 and aromatic amino acids improves each of the muscle mass, the gait speed and the grip strength more than the effects of each of the two components alone and also the additive effects of the two components alone.

The combination of the functional vitamin B6 with aromatic amino acids result in a P-value of 0.0102 in the outcome variable of muscle mass (D3Creatine/height^2); a P-value of 0.0006 in the outcome variable of gait speed; and a P-value of 0.3369 in the outcome variable of grip strength, as shown in Tables 2-4. These test results clearly demonstrated that the combination of the functional vitamin B6 and Trp improves each of the muscle mass and the gait speed more than the effects of each of the two components alone and also the additive effects of the two components alone.

The combination of the functional vitamin B6 and Phe result in a P-value of 0.0561 in the outcome variable of muscle mass (D3Creatine/height^2); a P-value of 0.1567 in the outcome variable of gait speed; and a P-value of 0.0109 in the outcome variable of grip strength, as shown in Tables 2-4. These test results clearly demonstrated that the combination of the functional vitamin B6 and Phe improves each of the muscle mass and the muscle grip strength more than the effects of each of the two components alone and also the additive effects of the two components alone.

The combination of the functional vitamin B6 and Tyr result in a P-value of 0.0343 in the outcome variable of muscle mass (D3Creatine/height^2); a P-value of 0.0573 in the outcome variable of gait speed; and a P-value of 0.0353 in the outcome variable of grip strength, as shown in Tables 2-4. These test results clearly demonstrated that the combination of the functional vitamin B6 and Tyr improves each of the muscle mass, the gait speed and the grip strength more than the effects of each of the two components alone and also the additive effects of the two components alone.

From the test results in Tables 2-4, the present inventors surprisingly found that there is a strong synergistic effects between the functional vitamin B6 with a combination of aromatic amino acids in improving the muscle mass, the gait speed and the grip strength. The present inventors also surprisingly found a strong synergistic effects between the functional vitamin B6 and Trp in improving the muscle mass and the gait speed; between the functional vitamin B6 and Phe in improving the muscle mass and the grip strength; and between the functional vitamin B6 and Tyr in improving the muscle mass, the gait speed and the grip strength.

From the test results in Tables 2-4, the present inventors also found that there was no significant synergistic effects between the functional vitamin B6 with any of the branched chain amino acids, Leu, Ile and Val; and further there is no significant synergistic effects between the functional vitamin B6 and the aromatic amino acids, His at the tested concentration range.

TABLE 2

Likelihood ratio tests for multiple regression models with and without interaction term between the functional vitamin B6 and an amino acid. Outcome variable: muscle mass (D3Creatine/height^2).

|  | L.R. Chisq | d.f. | P |
| --- | --- | --- | --- |
| AromAA | 5.64 | 1 | 0.0175 |
| Trp | 6.60 | 1 | 0.0102 |
| Phe | 3.65 | 1 | 0.0561 |
| Tyr | 4.48 | 1 | 0.0343 |
| His | 0.58 | 1 | 0.4451 |
| Leu | 2.11 | 1 | 0.1459 |
| Ile | 0.05 | 1 | 0.8245 |
| Val | 2.68 | 1 | 0.1014 |

TABLE 3

Likelihood ratio tests for multiple regression models with and without interaction term between the functional vitamin B6 and an amino acid. Outcome variable: gait speed.

|  | L.R. Chisq | d.f. | P |
| --- | --- | --- | --- |
| AromAA | 4.48 | 1 | 0.0342 |
| Trp | 11.68 | 1 | 0.0006 |
| Phe | 2.01 | 1 | 0.1567 |
| Tyr | 3.61 | 1 | 0.0573 |
| His | 1.21 | 1 | 0.2709 |
| Leu | 0.05 | 1 | 0.8162 |
| Ile | 0.59 | 1 | 0.4419 |
| Val | 0.14 | 1 | 0.7069 |

TABLE 4

Likelihood ratio tests for multiple regression models with and without interaction term between the functional vitamin B6 and an amino acid. Outcome variable: muscle grip strength.

|  | L.R. Chisq | d.f. | P |
| --- | --- | --- | --- |
| AromAA | 4.62 | 1 | 0.0316 |
| Trp | 0.92 | 1 | 0.3369 |
| Phe | 6.48 | 1 | 0.0109 |
| Tyr | 4.43 | 1 | 0.0353 |
| His | 1.88 | 1 | 0.1703 |
| Leu | 2.51 | 1 | 0.1133 |
| Ile | 1.25 | 1 | 0.2636 |
| Val | 1.31 | 1 | 0.2525 |

FIGS. 1-4 are visual representations of selected models using partial effects plots. These plots were generated by holding other predictors constant at their mean or any relevant value and plotting predictions of the outcome variable from the fitted model for various values of the predictor of interest (here one amino acid). The partial effects plot in FIG. 1 demonstrates the association between muscle mass and the sum of the aromatic amino acid concentrations (AAA) for different level of the functional vitamin B6 at mean age. The interaction term between the functional vitamin B6 and AAA is significant, and indeed the lines representing the association between muscle mass and aromatic AA concentration at constant age for increasing level of the functional vitamin B6 have increasing slopes.

Figure 2:
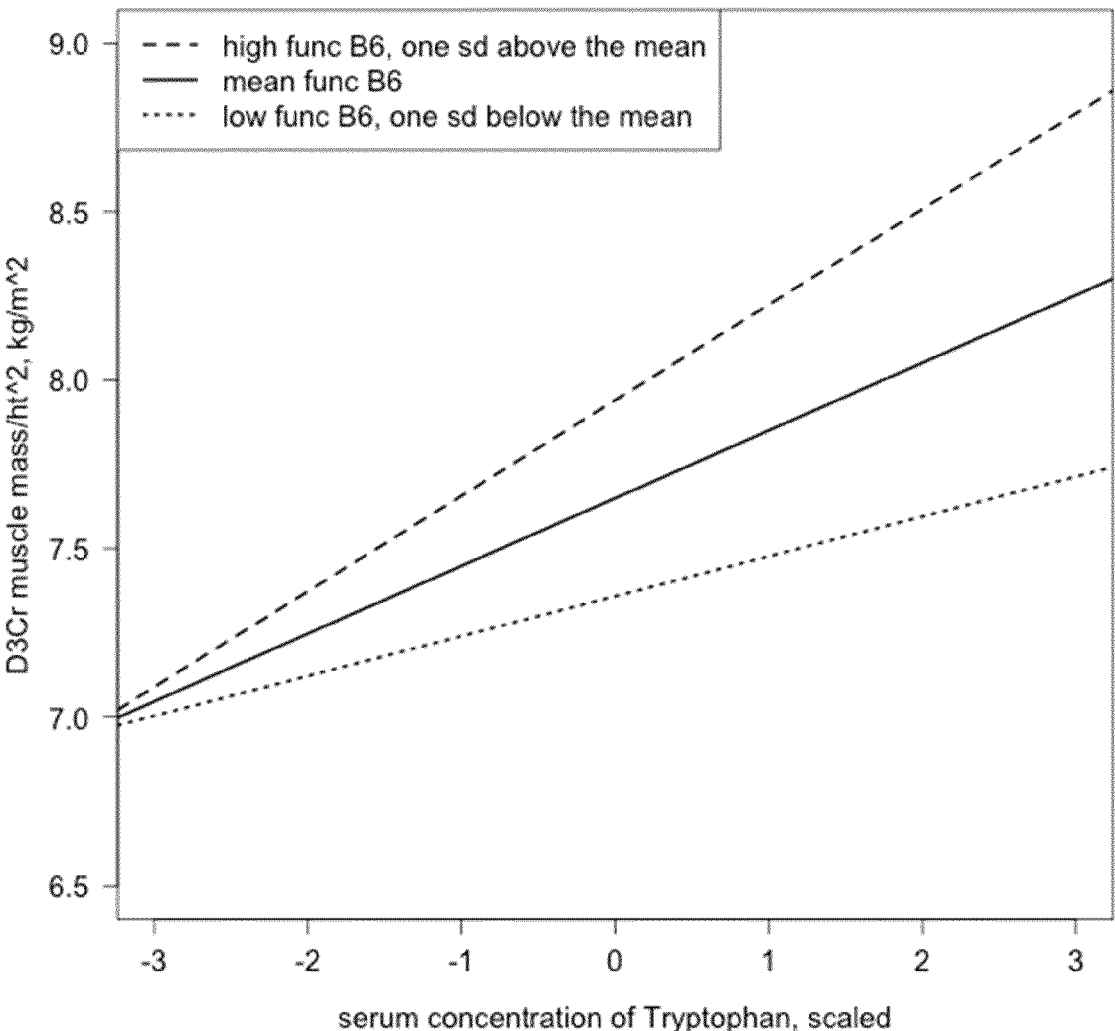
FIG. 2 shows the partial effects plot of association between muscle mass measured by the D3 creatine dilution method and serum Tryptophan concentration for different level of serum functional vitamin B6 (HK/XA) at mean age. The interaction term between functional vitamin B6 and Tryptophan (Trp) is significant and indeed the lines representing the association between muscle mass and Tryptophan concentration at constant age for increasing level of functional vitamin B6 have increasing slopes in Example 1 disclosed herein.

The partial effects plot in FIG. 2 demonstrates the association between muscle mass and Tryptophan (Trp) concentration for different level of the functional vitamin B6 at mean age. The interaction term between the functional vitamin B6 and Tryptophan is significant and indeed the lines representing the association between muscle mass and Tryptophan concentration at constant age for increasing level of the functional vitamin B6 have increasing slopes.

Figure 3:
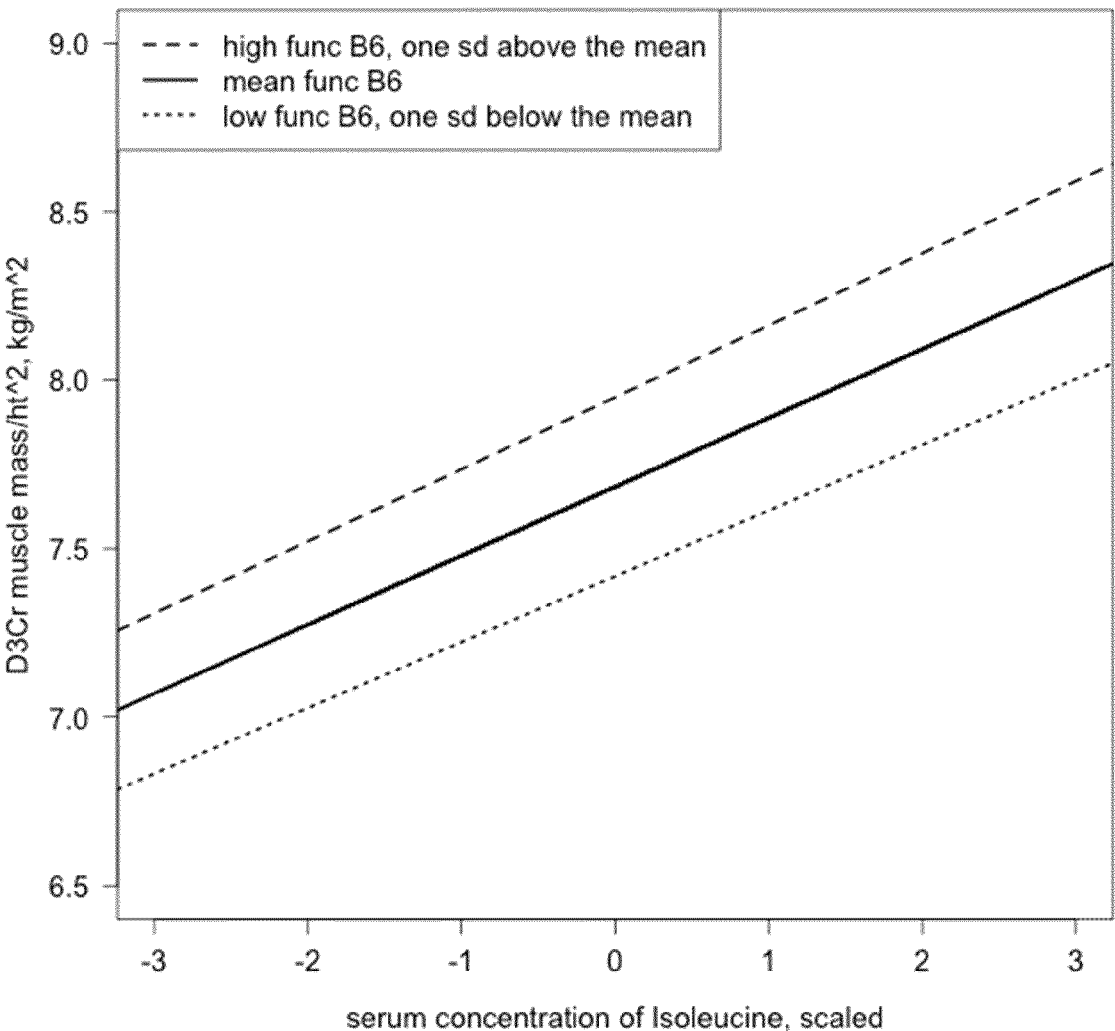
FIG. 3 shows the partial effects plot of association between measured by the D3 creatine dilution method muscle mass and serum Isoleucine concentration for different level of serum functional vitamin B6 (HK/XA) at mean age. The interaction term between functional vitamin B6 and Isoleucine (Ile) is not significant and indeed the lines representing the association between muscle mass and Isoleucine concentration for different level of functional vitamin B6 for the same age have the same slopes in Example 1 disclosed herein.

The partial effects plot in FIG. 3 demonstrates the association between muscle mass and Isoleucine concentration for different level of the functional vitamin B6 at mean age. The interaction term between the functional vitamin B6 and Isoleucine is not significant and indeed the lines representing the association between muscle mass and Isoleucine concentration for different level of the functional vitamin B6 for the same age have the same slopes.

Figure 4:
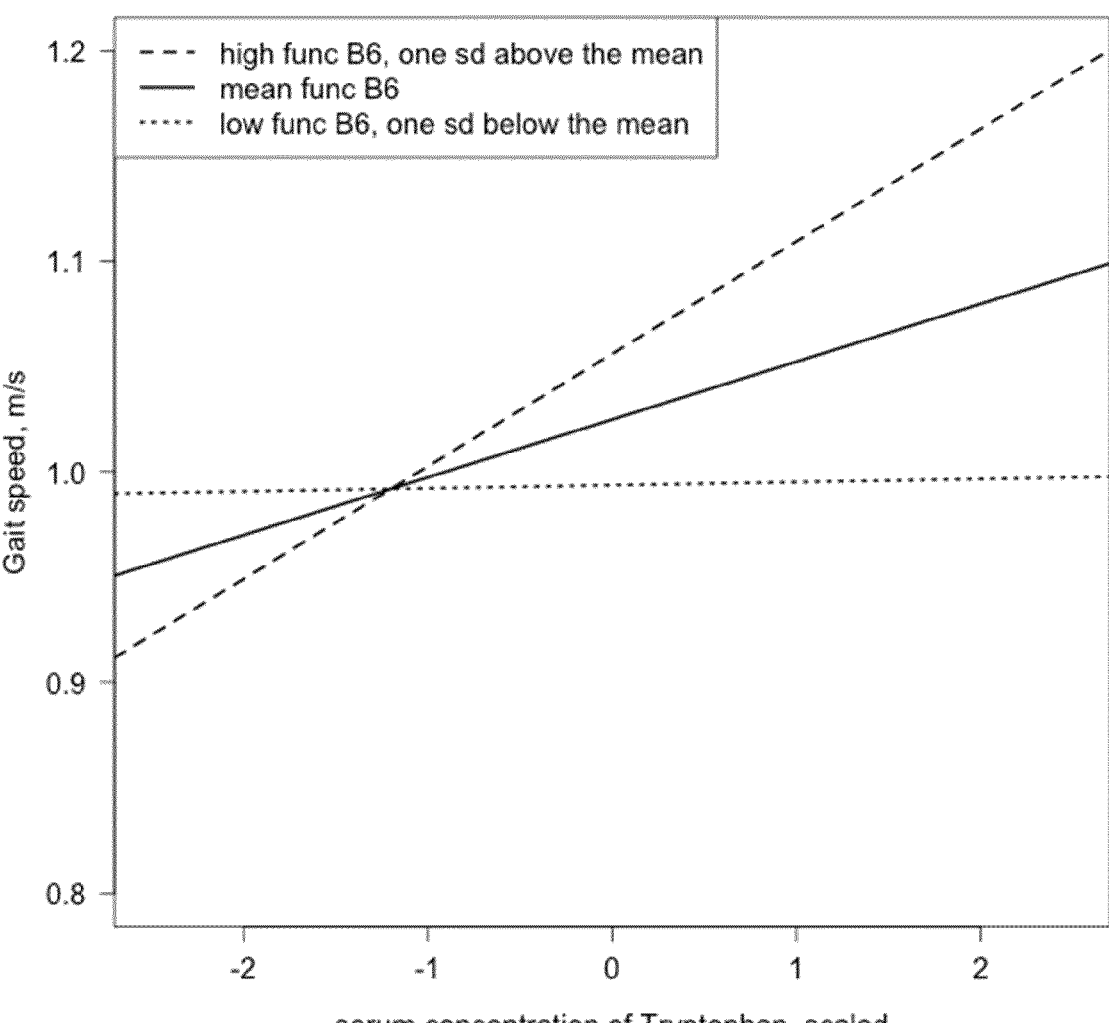
FIG. 4 shows the Partial effects plot of association between gait speed and serum Tryptophan concentration for different level of serum functional vitamin B6 (HK/XA) at mean age. The interaction term between functional vitamin B6 and Tryptophan is significant and indeed the lines representing the association between muscle mass and Tryptophan concentration at constant age for increasing level of functional vitamin B6 have increasing slopes in Example 1 disclosed herein.

The partial effects plot in FIG. 4 demonstrated the association between gait speed and Tryptophan concentration for different level of the functional vitamin B6 at mean age. The interaction term between the functional vitamin B6 and Tryptophan is significant and indeed the lines representing the association between muscle mass and Tryptophan concentration at constant age for increasing level of the functional vitamin B6 have increasing slopes.

Figure 5:
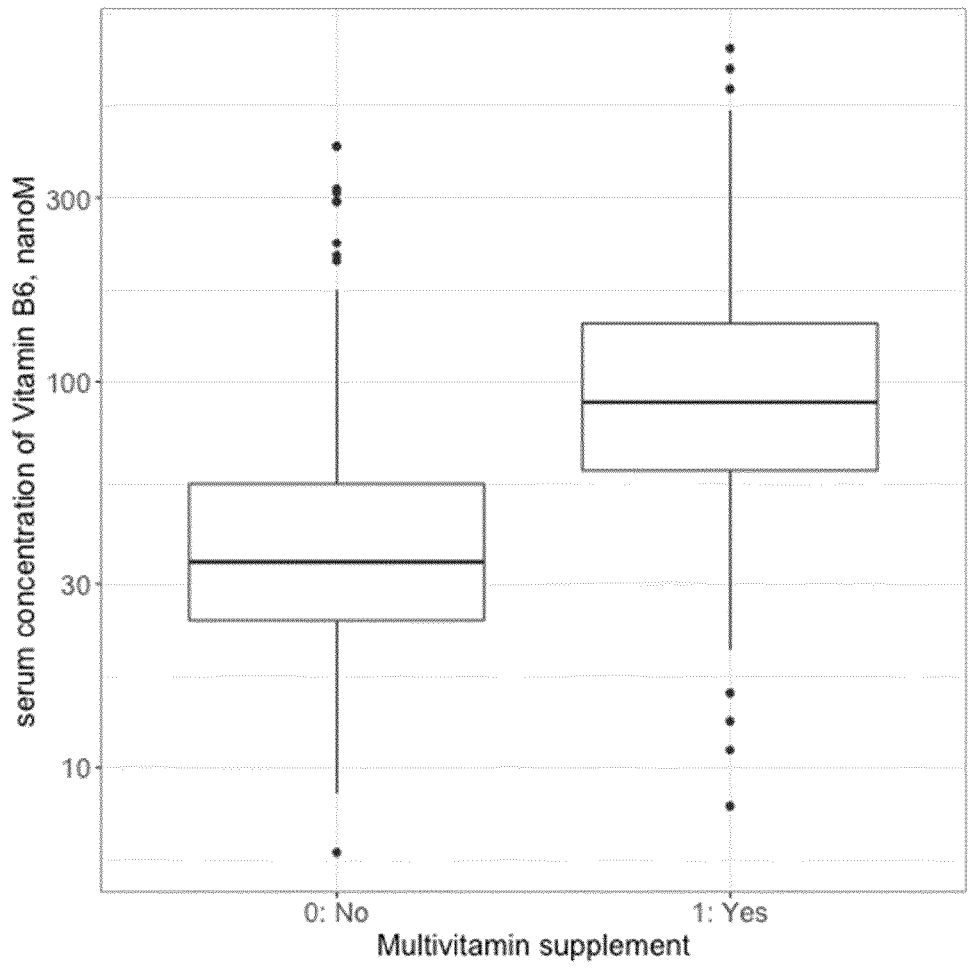
FIG. 5 shows boxplots of serum concentration of Vitamin B6 (PLP) for subjects reporting or not to take multivitamin supplement (Wilcoxon's test p-value 1.7 10^-35).

FIG. 5 Boxplot representing vitamin B6 (PLP) levels in serum per category of subjects reporting multivitamin supplement assumption, Wilcoxon rank sum test p-value=2.4*10^-39. The boxes represent the IQR, with the median indicated as a bar within the box. The whiskers represent 1.5 times the IQR (3rd quartile-1st quartile), outliers are indicated as circles. This example demonstrates that oral vitamin supplementation increases serum vitamin B6 levels.

Figure 6:
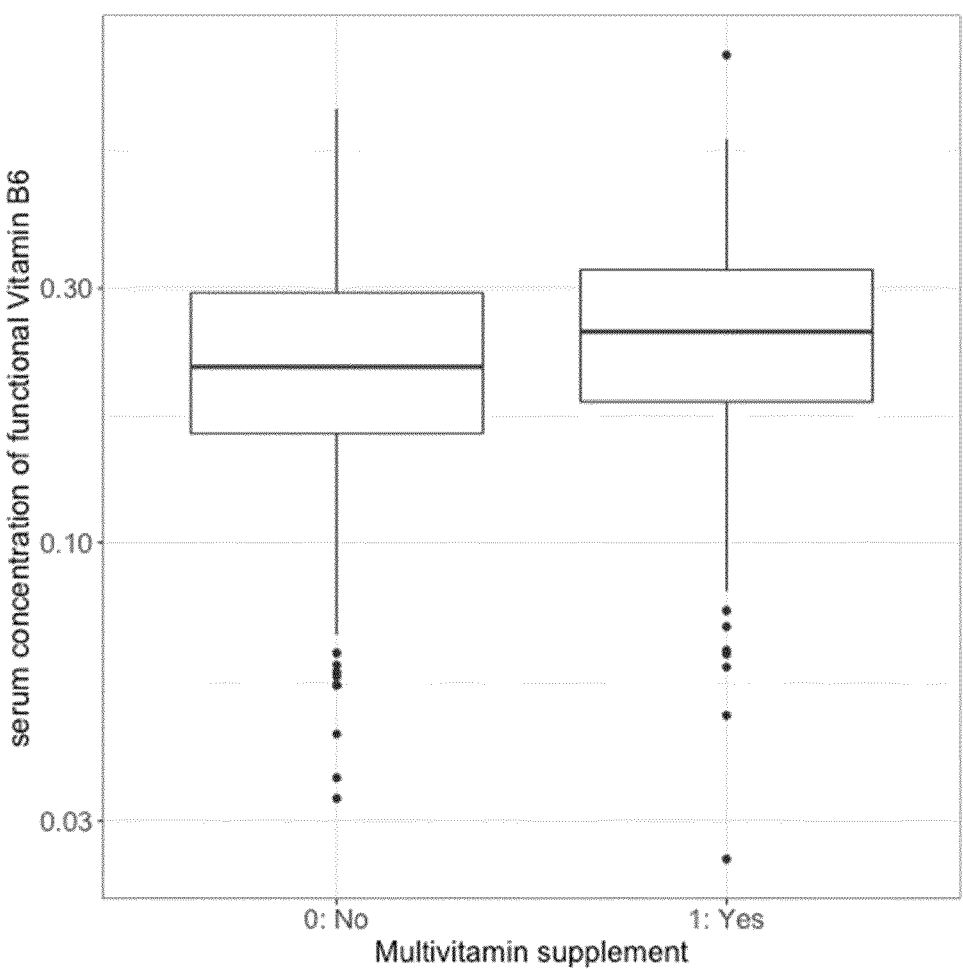
FIG. 6 shows boxplots of serum concentration of functional Vitamin B6 (HK/XA) for subjects reporting or not to take multivitamin supplement (Wilcoxon's test p-value 2.5 10^-3).
Figure 7:
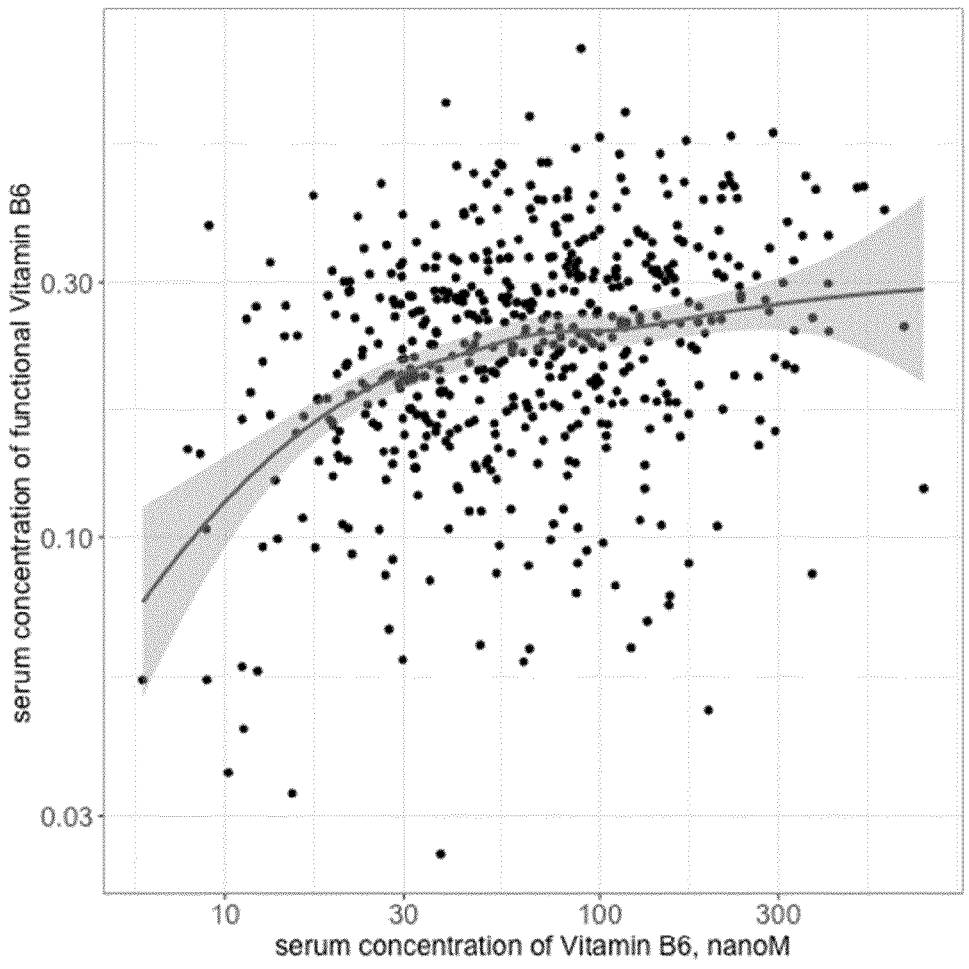
FIG. 7 is a scatter plot of serum concentration of Vitamin B6 (PLP) and functional Vitamin B6 (HK/XA)—Spearman rank correlation 0.31; p-value 6.2 10^-13.

FIG. 6: Boxplot representing functional vitamin B6 (HK/XA) levels in serum per category of subjects reporting multivitamin supplement assumption Wilcoxon rank sum test p-value=0.0039. The boxes represent the IQR, with the median indicated as a bar within the box. The whiskers represent 1.5 times the IQR (3rd quartile-1st quartile), outliers are indicated as circles. This example demonstrates that oral vitamin supplementation increases functional vitamin B6 levels FIG. 7: Association of functional vitamin B6 (HK/XA) with vitamin B6 (PLP), Spearman's rank correlation rho=0.31 p-value=6.3*10^-13. The blue line represents a local regression (loess method) and the gray-shaded areas indicate the 95% CI. This example demonstrates that increasing serum vitamin B6 levels increases functional vitamin B6 levels.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for preventing and/or treating sarcopenia and/or for improving skeletal muscle mass, skeletal muscle lean mass, skeletal muscle strength and/or skeletal muscle function in an individual in need thereof, the method comprising administering to the individual a unit dosage form of a composition comprising (i) one or more aromatic amino acids (AAAs) in a therapeutically effective amount and (ii) vitamin B6 in an amount of 1.0-12.0 mg/300.0 Kcal of energy of the composition, wherein the one or more aromatic amino acids are a combination of aromatic amino acids (AAAs) of Trp, Phe, Tyr and His; and daily dosages of total AAAs, the Trp, the Tyr, the Phe and the His are 3.0-20.0 g/day, 0.2-3.0 g/day, 1.5-8.8 g/day, 1.5-10.7 g/day and 0.9-5.6 g/day respectively.

2. The method of claim 1, wherein the one or more aromatic amino acids are selected from the group consisting of tryptophan (Trp), phenylalanine (Phe), tyrosine (Tyr), histidine (His) and combinations thereof.

3. The method of claim 1, wherein the unit further comprises EAAS and/or BCAAs selected from the group consisting of methionine (Met), lysine (Lys), valine (Val), leucine (Leu), Isoleucine (Ile), Threonine (Thr), and combinations thereof.

4. The method of claim 1, wherein the composition is in a form selected from the group consisting of an oral nutritional composition, a nutritional supplement, an oral nutritional supplement, a medical food, a food supplement, a food product, and a food for special medical purpose (FSMP).

5. The method of claim 1, wherein the composition is in a form selected from the group consisting of a solid powder, a powdered stick, a capsule and a solution.

6. A method of preventing or treating sarcopenia in an individual in need thereof, the method comprising administering a composition containing (i) a therapeutically effective amount of one or more aromatic amino acids and (ii) vitamin B6 in an amount of 1.0-12.0 mg/300.0 Kcal of energy of the composition, wherein the one or more aromatic amino acids are a combination of aromatic amino acids (AAAs) of Trp, Phe, Tyr and His; and daily dosages of total AAAs, the Trp, the Tyr, the Phe and the His are 3.0-20.0 g/day, 0.2-3.0 g/day, 1.5-8.8 g/day, 1.5-10.7 g/day and 0.9-5.6 g/day respectively.

7. A method for restoring and/or correcting deficiencies of nutrients in a subject having sarcopenia or at risk thereof, the method comprising administering a composition containing (i) a therapeutically effective amount of one or more aromatic amino acids and (ii) vitamin B6 in an amount of 1.0-12.0 mg/300.0 Kcal of energy of the composition, wherein the one or more aromatic amino acids are a combination of aromatic amino acids (AAAs) of Trp, Phe, Tyr and His; and daily dosages of total AAAs, the Trp, the Tyr, the Phe and the His are 3.0-20.0 g/day, 0.2-3.0 g/day, 1.5-8.8 g/day, 1.5-10.7 g/day and 0.9-5.6 g/day respectively.

8. The method of claim 7, wherein the one or more aromatic amino acids are selected from the group consisting of tryptophan (Trp), phenylalanine (Phe), tyrosine (Tyr), histidine (His) and combinations thereof.

9. The method of claim 7, wherein the composition further comprises EAAS and/or BCAAs selected from the group consisting of methionine (Met), lysine (Lys), valine (Val), leucine (Leu), Isoleucine (Ile), Threonine (Thr), and combinations thereof.

10. The method of claim 7, wherein the composition is administered in a daily dose comprising 1.0-25.0 mg vitamin B6 per day.

11. The method of claim 1, wherein the composition is administered in a daily dose comprising 1.0-25.0 mg vitamin B6 per day.

12. The method of claim 6, wherein the composition is administered in a daily dose comprising 1.0-25.0 mg vitamin B6 per day.

* * * * *